United States Patent [19]
Cheng et al.

[11] Patent Number: 6,080,566
[45] Date of Patent: Jun. 27, 2000

[54] ENZYMATIC DETOXIFICATION OF ORGANOPHOSPHORUS COMPOUNDS

[75] Inventors: Tu-Chen Cheng, Timonium; Joseph J. DeFrank, Bel Air, both of Md.

[73] Assignee: The United States of America as represented by the Secretary of the Army, Washington, D.C.

[21] Appl. No.: 09/243,934

[22] Filed: Feb. 4, 1999

Related U.S. Application Data

[62] Division of application No. 08/796,488, Feb. 6, 1987, Pat. No. 5,928,927
[60] Provisional application No. 06/015,966, Apr. 16, 1996.
[51] Int. Cl.$^7$ .............................. C12N 9/16; C12N 15/55; C12N 15/70; B09B 3/00
[52] U.S. Cl. ..................... 435/196; 435/262.5; 435/69.1; 435/252.3; 435/320.1; 514/2; 424/94.6
[58] Field of Search ................................ 435/196, 262.5; 514/2; 424/94.6

[56] References Cited

U.S. PATENT DOCUMENTS 5,928,927  7/1999  Cheng et al. ........................... 435/196

OTHER PUBLICATIONS

Chettur, G., et al., Fundamental and Applied Toxicology, vol. 11, "Soman–hydrolyzing and –detoxifying properties of an enzyme from a thermophilic bacterium", pp. 373–380, 1988.

Landis, W.G., et al., "Discovery of Multiple Organofluorophosphate Hydrolyzing Activities in the Protozoan Tetrahymena Thermophila". J.Appl. Toxicol., vol. 7, pp.35–41 (1987).

DeFrank, J.J., et al, "Screening of Halophilic Bacteria and Alteromonas Species for Organophosphorus Hydrolyzing Enzyme Activity". Chem. Biol.Interact., vol.87, pp.141–148, 1993.

McDaniel, C.S. et al., "Cloning and Sequencing of a Plasmid–Borne Gene (opd) Encoding a Phosphotriesterase", J. Bacteriol., vol. 170;, pp. 2306–2311, 1989.

Mulbry, W. &Karns, J., "Parathion Hydrolase Gene Specified by the Flavobacterium opd gene: Relationship Between the Gene and Protein", J.Bacteriol., vol. 171, pp. 6740–6746, 1989.

DeFrank J.J. & T.C. Cheng, "Purification and Properties of an Organophosphorus Acid Anhydrase from a Halophilic Bacterial Isolate", J.ofBacteriol., vol. 173, pp. 1938–1943, 1991.

Davis, et al., Basic Methods in Molecular Biology, p. 44–46, Elsevier, New York, 1986.

Short, J.M., et al., "Λ ZAP: A Bacteriophase ΛExpression Vection with in vivo Excision Properties", Nucleic Acids Res., vol. 16, pp. 7583–7589, 1988.

Cheng, T.C., et al., "Cloning and Expression of a Gene Encoding a Bacterial Enzyme for Decontamination of Organophosphorus Nerve Agents and Nucleotide Sequence of the Enzyme". Applied and Environmental Microbiology, vol. 62, pp. 1636–1641, May 1996.

Cheng, T.C. et al., "Purification and Properties of a Highly Active Organophosphorus Acid Anhydrolase from Alteromonas undina", Applied and Environmental Microbiology, vol. 59, pp. 3138–3140, Sep. 1993.

*Primary Examiner*—Ponnathapu Achutamurthy
*Assistant Examiner*—William W. Moore
*Attorney, Agent, or Firm*—Ulysses John Biffoni

[57] ABSTRACT

Compositions and methods are provided for enzymatic detoxification of organophosphorus compounds. The compositions contain a recombinant enzyme expressed by a cloned gene encoding an organophosphorus acid anhydrolase (OPAA-2) from the Alteromonas sp. bacteria, strain JD6.5. These compositions may be prepared as a dry powder and reconstituted with various water sources when needed. The methods involve application of compositions of recombinant OPAA-2 to surfaces or substances contaminated with organophosphorus compounds under conditions which maximize activity and stability of the enzyme.

21 Claims, 2 Drawing Sheets

SEQUENCE LISTING

```
(1) GENERAL INFORMATION:

(iii) NUMBER OF SEQUENCES: 2

(2) INFORMATION FOR SEQ ID NO:1:

(i) SEQUENCE CHARACTERISTICS:
       (A) LENGTH: 1740 base pairs
       (B) TYPE: nucleic acid
       (C) STRANDEDNESS: double
       (D) TOPOLOGY: linear (ii) MOLECULE TYPE: DNA (genomic)

(iii) HYPOTHETICAL: NO (iv) ANTI-SENSE: NO (vi) ORIGINAL SOURCE:
        (A) ORGANISM: Alteromonas sp.
        (B) STRAIN: JD6.5
```

(vii) IMMEDIATE SOURCE:
    (B) CLONE: pTC6513

(ix) FEATURE:
    (A) NAME/KEY: -10_signal
    (B) LOCATION: 14..18

(ix) FEATURE:
    (A) NAME/KEY: RBS
    (B) LOCATION: 24..30

(ix) FEATURE:
    (A) NAME/KEY: CDS
    (B) LOCATION: 36..1586

(xi) SEQUENCE DESCRIPTION: SEQ ID NO:1:

```
CTGCAGTTAA TAATATTTAG CAAAGTGGGT GATAC ATG AAT AAA TTA GCG GTG            53
                                       Met Asn Lys Leu Ala Val
                                        1               5

TTA TAC GCT GAA CAT ATT GCA ACC TTG CAA AAG CGC ACG CGC GAA ATT          101
Leu Tyr Ala Glu His Ile Ala Thr Leu Gln Lys Arg Thr Arg Glu Ile
         10                  15                  20

ATC GAG CGC GAA AAC CTA GAC GGT GTT GTT TTC CAT TCT GGC CAG GCG          149
Ile Glu Arg Glu Asn Leu Asp Gly Val Val Phe His Ser Gly Gln Ala
                 25                  30                  35

AAG CGC CAG TTC TTA GAC GAT ATG TAC TAC CCG TTT AAG GTG AAT CCA          197
Lys Arg Gln Phe Leu Asp Asp Met Tyr Tyr Pro Phe Lys Val Asn Pro
     40                  45                  50

CAA TTT AAG GCC TGG TTG CCA GTG ATA GAT AAT CCA CAC TGT TGG ATT          245
Gln Phe Lys Ala Trp Leu Pro Val Ile Asp Asn Pro His Cys Trp Ile
 55                  60                  65                  70

GTC GCG AAT GGC ACT GAT AAG CCA AAG TTG ATT TTC TAT CGC CCT GTG          293
Val Ala Asn Gly Thr Asp Lys Pro Lys Leu Ile Phe Tyr Arg Pro Val
                 75                  80                  85

GAC TTT TGG CAC AAG GTC CCC GAT GAG CCG AAT GAG TAT TGG GCT GAC          341
Asp Phe Trp His Lys Val Pro Asp Glu Pro Asn Glu Tyr Trp Ala Asp
             90                  95                 100

TAC TTT GAT ATT GAA CTG CTA GTG AAA CCG GAT CAG GTA GAA AAG TTA          389
Tyr Phe Asp Ile Glu Leu Leu Val Lys Pro Asp Gln Val Glu Lys Leu
         105                 110                 115

CTA CCC TAT GAT AAG GCG CGA TTT GCA TAT ATT GGC GAA TAC TTG GAA          437
Leu Pro Tyr Asp Lys Ala Arg Phe Ala Tyr Ile Gly Glu Tyr Leu Glu
120                 125                 130

GTC GCT CAA GCT TTG GGT TTT GAG CTG ATG AAT CCG GAG CCG GTA ATG          485
Val Ala Gln Ala Leu Gly Phe Glu Leu Met Asn Pro Glu Pro Val Met
135                 140                 145                 150

AAC TTT TAT CAT TAC CAC CGT GCC TAC AAA ACG CAG TAC GAA CTT GCT          533
Asn Phe Tyr His Tyr His Arg Ala Tyr Lys Thr Gln Tyr Glu Leu Ala
                 155                 160                 165

TGT ATG CGT GAG GCG AAT AAA ATC GCT GTA CAA GGT CAC AAA GCT GCG          581
Cys Met Arg Glu Ala Asn Lys Ile Ala Val Gln Gly His Lys Ala Ala
             170                 175                 180

CGA GAT GCG TTT TTT CAA GGC AAG TCC GAA TTT GAA ATT CAA CAA GCC          629
Arg Asp Ala Phe Phe Gln Gly Lys Ser Glu Phe Glu Ile Gln Gln Ala
         185                 190                 195

TAC CTG TTA GCG ACC CAA CAC AGC GAA AAT GAC AAC GCT TAC GGC AAC          677
Tyr Leu Leu Ala Thr Gln His Ser Glu Asn Asp Asn Ala Tyr Gly Asn
200                 205                 210

ATT GTG GCG CTA AAT GAA AAC TGC GCC ATT TTG CAC TAC ACG CAC TTT          725
Ile Val Ala Leu Asn Glu Asn Cys Ala Ile Leu His Tyr Thr His Phe
215                 220                 225                 230

GAT CGT GTT GCT CCT GCT ACC CAT CGT TCT TTT TTG ATT GAC GCT GGC          773
Asp Arg Val Ala Pro Ala Thr His Arg Ser Phe Leu Ile Asp Ala Gly
```

```
                     235                  240                   245
GCC AAC TTC AAT GGT TAC GCA GCC GAT ATT ACT CGA ACC TAT GAC TTT      821
Ala Asn Phe Asn Gly Tyr Ala Ala Asp Ile Thr Arg Thr Tyr Asp Phe
            250                 255                 260

ACT GGT GAA GGG GAA TTT GCT GAG CTT GTT GCC ACC ATG AAG CAG CAC      869
Thr Gly Glu Gly Glu Phe Ala Glu Leu Val Ala Thr Met Lys Gln His
            265                 270                 275

CAA ATT GCA CTA TGT AAC CAG TTG GCG CCT GGC AAG TTA TAT GGT GAG      917
Gln Ile Ala Leu Cys Asn Gln Leu Ala Pro Gly Lys Leu Tyr Gly Glu
            280                 285                 290

TTA CAC CTT GAT TGT CAC CAA CGT GTG GCG CAA ACA CTG AGT GAC TTT      965
Leu His Leu Asp Cys His Gln Arg Val Ala Gln Thr Leu Ser Asp Phe
295                 300                 305                 310

AAC ATC GTC GAC TTA TCG GCC GAT GAG ATT GTT GCC AAA GGC ATT ACC     1013
Asn Ile Val Asp Leu Ser Ala Asp Glu Ile Val Ala Lys Gly Ile Thr
            315                 320                 325

TCC ACG TTC TTC CCA CAT GGT TTA GGC CAT CAT ATT GGT TTA CAA GTA     1061
Ser Thr Phe Phe Pro His Gly Leu Gly His His Ile Gly Leu Gln Val
            330                 335                 340

CAT GAT GTG GGT GGT TTT ATG GCT GAC GAG CAG GGC GCA CAC CAA GAG     1109
His Asp Val Gly Gly Phe Met Ala Asp Glu Gln Gly Ala His Gln Glu
            345                 350                 355

CCG CCT GAA GGT CAC CCA TTC CTG CGT TGC ACG CGT AAG ATT GAA GCG     1157
Pro Pro Glu Gly His Pro Phe Leu Arg Cys Thr Arg Lys Ile Glu Ala
            360                 365                 370

AAT CAA GTA TTT ACC ATT GAA CCT GGG TTG TAC TTT ATT GAT TCC TTG     1205
Asn Gln Val Phe Thr Ile Glu Pro Gly Leu Tyr Phe Ile Asp Ser Leu
375                 380                 385                 390

CTC GGT GAT TTA GCA GCG ACA GAT AAT AAT CAG CAT ATT AAT TGG GAC     1253
Leu Gly Asp Leu Ala Ala Thr Asp Asn Asn Gln His Ile Asn Trp Asp
            395                 400                 405

AAG GTC GCA GAG CTT AAG CCT TTC GGT GGT ATT CGT ATT GAG GAC AAT     1301
Lys Val Ala Glu Leu Lys Pro Phe Gly Gly Ile Arg Ile Glu Asp Asn
            410                 415                 420

ATC ATT GTT CAC GAA GAC AGC CTT GAG AAT ATG ACT CGC GAG CTA AGA     1349
Ile Ile Val His Glu Asp Ser Leu Glu Asn Met Thr Arg Glu Leu Arg
            425                 430                 435

GCT CGA TTA ACC ACC CAT TCA CTG CGG GGC CTA AGT GCT CCG CAG TTT     1397
Ala Arg Leu Thr Thr His Ser Leu Arg Gly Leu Ser Ala Pro Gln Phe
            440                 445                 450

TCT ATC AAT GAT CCT GCC GTT ATG TCT GAA TAC TCA TAC CCT AGT GAG     1445
Ser Ile Asn Asp Pro Ala Val Met Ser Glu Tyr Ser Tyr Pro Ser Glu
455                 460                 465                 470

CCC TTA AGT TAC GAA GAA GAA ATC AAA AAG AGC ACT TTT ATT GTG CAT     1493
Pro Leu Ser Tyr Glu Glu Glu Ile Lys Lys Ser Thr Phe Ile Val His
            475                 480                 485

GTG CGC ACA CGC CGG ATA TTA GTG CGG CGA AGG ACT TTA TCG CCG ATA     1541
Val Arg Thr Arg Arg Ile Leu Val Arg Arg Arg Thr Leu Ser Pro Ile
            490                 495                 500

TTA ATC GCC GTT ACC CCG ATG CCC GCC ATA ACT GCT GGG CTC ATG         1586
Leu Ile Ala Val Thr Pro Met Pro Ala Ile Thr Ala Gly Leu Met
            505                 510                 515

TAGCAGGGGC TCCAGGAGGC AGCCATGTGT ATGGCTTTTC CGATGATGGC GAGCCCAATG   1646

GGACTGCTGG CAAACCAATG CTGAATGTGC TCCAAGGCAG TGGCCTTGGC GAAATTTGTG   1706

CTGTGACAAC GCGTTACTTC GGTGGTATTA AGCT                               1740

(2) INFORMATION FOR SEQ ID NO:2:
```

-continued (i) SEQUENCE CHARACTERISTICS:
    (A) LENGTH: 517 amino acids
    (B) TYPE: amino acid
    (D) TOPOLOGY: linear (ii) MOLECULE TYPE: protein (xi) SEQUENCE DESCRIPTION: SEQ ID NO:2:

Met Asn Lys Leu Ala Val Leu Tyr Ala Glu His Ile Ala Thr Leu Gln
 1               5                  10                  15

Lys Arg Thr Arg Glu Ile Ile Glu Arg Glu Asn Leu Asp Gly Val Val
             20                  25                  30

Phe His Ser Gly Gln Ala Lys Arg Gln Phe Leu Asp Asp Met Tyr Tyr
         35                  40                  45

Pro Phe Lys Val Asn Pro Gln Phe Lys Ala Trp Leu Pro Val Ile Asp
 50                  55                  60

Asn Pro His Cys Trp Ile Val Ala Asn Gly Thr Asp Lys Pro Lys Leu
 65                  70                  75                  80

Ile Phe Tyr Arg Pro Val Asp Phe Trp His Lys Val Pro Asp Glu Pro
                 85                  90                  95

Asn Glu Tyr Trp Ala Asp Tyr Phe Asp Ile Glu Leu Leu Val Lys Pro
                100                 105                 110

Asp Gln Val Glu Lys Leu Leu Pro Tyr Asp Lys Ala Arg Phe Ala Tyr
            115                 120                 125

Ile Gly Glu Tyr Leu Glu Val Ala Gln Ala Leu Gly Phe Glu Leu Met
130                 135                 140

Asn Pro Glu Pro Val Met Asn Phe Tyr His Tyr His Arg Ala Tyr Lys
145                 150                 155                 160

Thr Gln Tyr Glu Leu Ala Cys Met Arg Glu Ala Asn Lys Ile Ala Val
                165                 170                 175

Gln Gly His Lys Ala Ala Arg Asp Ala Phe Phe Gln Gly Lys Ser Glu
            180                 185                 190

Phe Glu Ile Gln Gln Ala Tyr Leu Leu Ala Thr Gln His Ser Glu Asn
        195                 200                 205

Asp Asn Ala Tyr Gly Asn Ile Val Ala Leu Asn Glu Asn Cys Ala Ile
210                 215                 220

Leu His Tyr Thr His Phe Asp Arg Val Ala Pro Ala Thr His Arg Ser
225                 230                 235                 240

Phe Leu Ile Asp Ala Gly Ala Asn Phe Asn Gly Tyr Ala Ala Asp Ile
                245                 250                 255

Thr Arg Thr Tyr Asp Phe Thr Gly Glu Gly Glu Phe Ala Glu Leu Val
            260                 265                 270

Ala Thr Met Lys Gln His Gln Ile Ala Leu Cys Asn Gln Leu Ala Pro
        275                 280                 285

Gly Lys Leu Tyr Gly Glu Leu His Leu Asp Cys His Gln Arg Val Ala
290                 295                 300

Gln Thr Leu Ser Asp Phe Asn Ile Val Asp Leu Ser Ala Asp Glu Ile
305                 310                 315                 320

Val Ala Lys Gly Ile Thr Ser Thr Phe Phe Pro His Gly Leu Gly His
                325                 330                 335

His Ile Gly Leu Gln Val His Asp Val Gly Gly Phe Met Ala Asp Glu
            340                 345                 350

Gln Gly Ala His Gln Glu Pro Pro Glu Gly His Pro Phe Leu Arg Cys
        355                 360                 365

Thr Arg Lys Ile Glu Ala Asn Gln Val Phe Thr Ile Glu Pro Gly Leu

-continued

```
                        370                     375                     380
Tyr Phe Ile Asp Ser Leu Leu Gly Asp Leu Ala Ala Thr Asp Asn Asn
385                     390                     395                     400

Gln His Ile Asn Trp Asp Lys Val Ala Glu Leu Lys Pro Phe Gly Gly
                405                     410                     415

Ile Arg Ile Glu Asp Asn Ile Ile Val His Glu Asp Ser Leu Glu Asn
                420                     425                     430

Met Thr Arg Glu Leu Arg Ala Arg Leu Thr Thr His Ser Leu Arg Gly
            435                     440                     445

Leu Ser Ala Pro Gln Phe Ser Ile Asn Asp Pro Ala Val Met Ser Glu
        450                     455                     460

Tyr Ser Tyr Pro Ser Glu Pro Leu Ser Tyr Glu Glu Glu Ile Lys Lys
465                     470                     475                     480

Ser Thr Phe Ile Val His Val Arg Thr Arg Arg Ile Leu Val Arg Arg
                485                     490                     495

Arg Thr Leu Ser Pro Ile Leu Ile Ala Val Thr Pro Met Pro Ala Ile
                500                     505                     510

Thr Ala Gly Leu Met
            515
```

ENZYMATIC DETOXIFICATION OF ORGANOPHOSPHORUS COMPOUNDS

This application is a division of application Ser. No. 08/796,488, filed on Feb. 6, 1997, now issued as U.S. Pat. No. 5,928,927, which in turn is a nonprovisional continuation of provisional application Ser. No. 06/015,966, filed on Apr. 16. 1996.

GOVERNMENTAL INTEREST

The invention described herein may be manufactured, used and licensed by or for the U.S. Government.

FIELD OF THE INVENTION

The present invention relates generally to the hydrolysis of organophosphorus compounds. More specifically, the present invention relates to the expression of a recombinant bacterial enzyme which is useful for detoxifying cholinesterase-inhibiting organophosphorus compounds such as pesticides and chemical nerve agents and the decontamination of substances contaminated with these compounds.

BACKGROUND OF THE INVENTION

A number of organophosphorus (OP) compounds used by the agriculture industry and the military are highly toxic and thus hazardous to human health and harmful to the environment. For example, acetylcholinesterase-inhibiting OP compounds comprise the active ingredient of pesticides such as paraoxon as well as G-type nerve agents such as Sarin and Soman, etc., developed for chemical warfare. Thus, it is very important to be able to detoxify such OP compounds and to decontaminate surfaces and substances contaminated with these compounds.

Currently, the U.S. Army uses a nerve agent decontamination solution, DS2, which is composed (by weight) of 2% NaOH. 28% ethylene glycol monomethyl ether, and 70% diethylenetriamine (Richardson, G. A. "Development of a package decontamination system", EACR-1 310-17, U.S. Army Edgewood Arsenal Contract Report (1972), herein incorporated by reference). Although this decontamination solution is effective against nerve agents, it is quite toxic, flammable, corrosive, and can threaten the environment. Thus, there is a need for an alternative decontamination technology that is both effective and non hazardous to personnel. equipment, and/or the environment.

One approach being investigated as a potential solution to this problem is enzyme-mediated decontamination. For example, a class of enzymes known as organophosphorus acid (OPA) anhydrolases (OPAA) (EC 3.1.8.2) can catalyze the hydrolysis of a variety of OP compounds including pesticides and fluorinated "G-type" nerve agents. (See, e.g., Landis, W. G., et al., "Discovery of multiple organofluorophosphate hydrolyzing activities in the protozoan *Tetrahymena thermophila*", *J. Appi. Toxicol.*, Vol. 7, pp. 35–41, 1987; DeFrank, J. J., et al., "Screening of halophilic bacteria and alteromonas species for organophosphorus hydrolyzing enzyme activity", *Chem. Biol. Interact.*, Vol. 87, pp. 141–148, 1993; each of which is incorporated herein by reference.) Although OPA anhydrolases are produced by both prokaryotic and eukaryotic organisms, their use for enzymatic decontamination requires an abundant supply that is readily and cheaply obtained. Thus, a recombinant microorganism that is easily grown and capable of overexpressing an OPAA having high activity against cholinesterase-inhibiting OP compounds under a variety of conditions would be very desirable.

The first OP-hydrolyzing enzyme gene to be cloned, sequenced, and expressed was that for organophosphorus hydrolase (OPH) (EC 3.1.8.1), which is encoded by the opd gene of *Pseudomonas diminuta* MG and the Flavobacterium sp. strain ATCC 27551. (See, e.g., McDaniel, C.S. et al., "Cloning and sequencing of a plasmid-borne gene (opd) encoding a phosphotriesterase", *J. Bacteriol.*, Vol. 170:, pp. 2306–2311, 1989, incorporated herein by reference.) The open reading frame of the opd gene contains 975 bases which encode a polypeptide of 325 amino acid residues with a molecular mass of 35 kDa. (See Mulbry, W. and Karns, J., "Parathion hydrolase gene specified by the Flavobacterium opd gene: relationship between the gene and protein", *J. Bacteriol.*, Vol. 171, pp. 6740–6746, 1989, incorporated herein by reference.)

The inventors have recently purified another OPAA with very high OP-hydrolyzing activity from a bacteria strain, Alteromonas sp. strain JD6.5, isolated from Grantsville Warm Springs in Salt Lake City, Utah. (DeFrank J. J. and T.-C. Cheng, "Purification and properties of an organophosphorus acid anhydrolase from a halophilic bacterial isolate", *J. of Bacteriol.*, Vol. 173, pp. 1938–1943, 1991, herein incorporated by reference.) This enzyme, OPAA-2, displays high catalytic activity at a wide pH range (6.0 to 9.5) and temperature range (10° to 65° C.), with optimum activity at pH 8.5 and 50° C. OPAA-2 has hydrolytic activity against a number of OP compounds, including the chemical nerve agents Sarin (GB; o-isopropyl methylphosphonofluoridate), Soman (GD: o-pinacolylmethylphosphonofluoridate), and GF (o-cyclohexyl methylphosphonofluoridate), the nerve-agent-analog diisopropyl fluorophosphate (DFP), and pesticides such as paraoxon.

SUMMARY OF THE INVENTION

It is an object of the present invention to provide a system for enzymatic degradation of organophosphorus compounds that is simple and safe for users, equipment, and/or the environment.

It is another object of the present invention to provide a composition for enzymatic degradation of organophosphorus compounds that is compatible with a variety of foams, e.g., fire fighting foams, wetting agents, and degreasers.

These and other objects are satisfied by the present invention which concerns the cloning, sequencing and expression of the gene encoding OPAA-2 from Alteromonas sp. strain JD6.5.

Accordingly, the present invention includes an isolated and purified DNA fragment comprising a DNA sequence encoding a polypeptide having the biological activity of OPAA-2.

The invention also includes a recombinant DNA (rDNA) construct for expressing OPAA-2 in prokaryotic cells. The rDNA construct comprises a prokaryotic promoter operatively linked to a DNA sequence coding for a polypeptide having the biological activity of OPAA-2.

Another aspect of the present invention includes recombinant OPAA-2 (rOPAA-2) formulated for a long shelf life. In particular. the present invention provides rOPAA-2 as a dehydrated powder that can be reconstituted with various water sources.

Yet another aspect of the present invention is the use of rOPAA-2 to detoxify stocks of cholinesterase-inhibiting organophorus compounds, to decontaminate surfaces contaminated with these compounds, to remediate contaminated soils, and to treat liquid and solid wastes generated from producing these compounds.

BRIEF DESCRIPTION OF THE DRAWINGS

FIG. 1 shows the OPA anhydrolase activity of purified rOPAA-2 against substrates DFP, GB (Sarin), GD (Soman), GF (o-cyclohexyl methylphosphonofluoridate) and NP-GD (chromogenic soman analog).

FIG. 5 shows the effect on the specific activity of rOPAA-2 against DFP when lyophilized enzyme is reconstituted with different $(NH_4)_2CO_3$-buffered water sources containing no foam. 6% blast containment foam (AFC-300), or 6% fire-fighting foam (FFF).

DETAILED DESCRIPTION OF THE INVENTION

The present invention is based on the cloning and expression of the gene coding for OPAA-2 from Alteromonas sp. strain JD6.5, also referred to as opaA. To accomplish this, the following experiments were performed.

EXAMPLE 1

Cloning and Sequencing of opaA
Cultivation of Alteromonas sp. Strain JD6.5.

The A. sp. JD6.5 strain was grown in 10 ml of a medium consisting of the following (per liter): NaCl, 50 g; $MgSO_4 \cdot H_2O$. 10 g; Proteose peptone. 10 g; yeast extract, 6 g; and N-2-hydroxyethylpeperazine-N'-2-ethanesulfonic acid (HEPES), 2.5 g (pH 6.8). The 10 ml culture was incubated at 30–37° C., on a rotary shaker at 240 rpm, for 18 to 24 hours. The bacteria cells were then harvested by centrifugation (7,500×g) for 10 min, resuspended in 10 ml of phosphate-buffered saline (PBS) and then collected by centrifugation at 1,000×g for 5 min.
Construction of a Genomic Library Expressing OPAA-2.

High molecular weight genomic DNA from the above cultured cells of A. JD6.5 was prepared as described by Davis et al., Basic Methods in Molecular Biology, p. 44–46, Elsevier, N.Y., 1986, herein incorporated by reference. The genomic DNA was partially digested with EcoRI and the resulting 4–8 kb DNA fragments were size fractionated by agarose gel electrophoresis. The separated fragments were purified from the gel with the Geneclean™ II kit (Bio-101, La Jolla, Calif.). The purified DNA fragments were then ligated to EcoRI-digested, phosphatase-treated Lambda ZAP® arms obtained from Stratagene® (La Jolla, Calif.) and then packaged with Gigapack® II Gold packaging extract (Stratagene®). Host strain E. coli XL1-Blue (Stratagene®) was infected with the resulting recombinant phage preparation and plated onto LB agar plates.
Screening of Cloned OPAA-2.

To verify that the above genomic library contained OPAA-2 genomic DNA from A. sp. JD6.5, it was screened for the presence of recombinant plaques with an anti-OPAA-2 serum, the preparation of which has been described previously (DeFrank J. J. and T.-C. Cheng, 1991). Approximately $6 \times 10^4$ plaque-forming units (pfu) were plated at a density of $1.5 \times 10^4$ pfu per 90-mm-diameter plate on E. coli XL1-Blue cells. After 6 hours of growth at 37° C., the plates were overlaid with nitrocellulose filters saturated with 10 mM isopropyl-β-D-thiogalactopyranoside (IPTG), and incubated for an additional 3 h. After cooling at 4° C. for 1 h., the filters were then removed from the plates and blocked overnight at room temperature with TBS (50 mM Tris, pH 7.5, 150 mM NACl) containing 5% dry skim milk.

Immunodetection of OPAA-2 was carried out by first incubating the filters with a 1:2000 (v/v) dilution of anti-OPAA-2 serum in TBS for 1 h. After three washes in TBS, the filters were incubated with goat anti-rat IgG-alkaline phosphatase conjugate (Fisher Scientific, Pittsburgh, Pa.). Following 3 washes with TBS, the bound alkaline phosphatase was assayed with the substrate 5-bromo-4-chloro-3-indolyl phosphate/nitro blue tetrazolium (BCIP/NBT). Of $6 \times 10^4$ plaques examined, 5 clones gave strong signals with the anti-OPAA-2 serum.
Excision of Plasmid from the Lambda ZAP® Vector and Subcloning of the Cloned Gene.

The excision of plasmid from the positive clones was carried out as described by Short, J. M., et al., "λZAP: a bacteriophage λ expression vector with in vivo excision properties", Nucleic Acids Res., Vol. 16, pp. 7583–7589 (1988), incorporated herein by reference. The recovered plasmids all contained a 6.1 kb EcoRl DNA fragment.

One positive clone, designated pTC651, was chosen for subcloning. This plasmid was digested with PstI and then partially digested with HindIII. The purified PstI-HindIII fragments were subcloned into the PstI and HindIII sites of pBluescript® and the resulting recombinant plasmids used to transform Epicurian Coli® XL1-blue host cells using standard procedures (see e.g., Sambrook, J., et al., Molecular cloning: a laboratory manual. 2nd ed., Cold Spring Harbor Laboratory, Cold Spring Harbor, N.Y., 1989, incorporated herein by reference).

The resulting transformants were analyzed for the expression of functional rOPAA-2 by Western analysis and DFP-hydrolyzing activity as described by Cheng, T-C., et al., "Cloning, Expression and Nucleotide Sequence of a Bacterial Enzyme for Decontamination of Organophosphorus Nerve Agents", Applied and Environmental Microbiology, Vol. 62, pp. 1636–1641 (1996), incorporated herein by reference. The subclone, designated pTC6513, was found to contain the PstI-HindIII fragment, 1.74 kb in length, which encoded functional OPAA-2. Recombinant bacteria cells pTC6513/XL1-blue were deposited on 12118/96 with the ATCC (12301 Parklawn Drive, Rockville, Md. 10852) under Accession No. 98281.
DNA Sequencing of the OPA Anhydrolase Gene.

The nucleotide sequence of the PstI-HindIII fragment carried by pTC6513 was determined from both strands using the Taq cycle sequencing method and fluorescently-labeled T7 or T3 primers or, when sequence-specific primers were used, fluorescently-labeled dideoxynucleotides. The sequencing reactions were performed by an automated DNA sequencer, Model 373A (Perkin Elmer, Applied Biosystems Div.; Foster City, Calif.), following the manufacturer's protocol. Computer analysis of the obtained DNA sequence was performed with the MacVector® program version 4.1.4 (Kodak; New Haven, Conn.). The Genbank accession number of the OPAA-2 gene sequence is U29240.

The 1,740 base pair (bp) nucleotide sequence oriented from the PstI site to the HindIII site is shown in SEQ ID NO.: 1. Within this sequence, only one large open reading frame was found. This open reading frame, beginning at nucleotide 36 and terminating at nucleotide 1586, consisted of a 1,551 bp nucleotide sequence encoding a polypeptide of 517 amino acid residues having the deduced amino acid sequence shown in SEQ ID NO.: 2. The calculated molecular weight of this polypeptide is 59 kDa. which is very close to the 60 kDa molecular weight of native OPAA-2 determined by Western analysis.

As is well-known in the art, conservative changes may be made to either or both of the DNA and amino acid sequences of SEQ ID NO.: 1 and SEQ ID NO.: 2 without significantly affecting the biological activity of the expressed polypeptide. Accordingly, the present invention includes all DNA fragments having a DNA sequence which codes for a polypeptide having the biological activity of OPAA-2. These DNA fragments are identified as those that contain DNA sequences which are substantially homologous to the DNA sequence of SEQ ID NO.:1 or its complementary sequence.

Substantially homologous DNA sequences are defined as having at least about 85% homology over the defined length of the DNA sequences, with at least about 90% homology being preferred and at least about 95% homology being most preferred. Sequences that are substantially homologous may be identified in a Southern hybridization experiment under stringent conditions. Defining stringent conditions for a particular hybridization experiment is within the skill of the art. Generally, hybridization under stringent conditions is performed at about 5° C. lower than the thermal melting point for the specific sequence at a defined ionic strength and pH (T. Maniatis et al., Molecular Cloning, A Laboratory Manual, Cold Spring Harbor Laboratory (1982), pp. 387–389, incorporated herein by reference). Typical stringent conditions include hybridization in 4×SSC at 65° C. or in 4×SSC, 50% formamide at 42° C., followed by washing in 0.1×SSC at 65° for 30 min.

In addition, it is also well known in the art that a variety of prokaryotic promoters and host microorganisms are capable of expressing recombinant proteins. Accordingly, the present invention is not limited to the use of any particular combination of expression vector and host cell for expression of a DNA fragment comprising a DNA sequence coding for OPAA-2. For example, the following expression systems have been used to overexpress and purify rOPAA-2: pRSET Xpress® Kit (Cat. #K880-01, Invitrogen, San Diego, Calif.); pProEX HT® Protein Expression System (Cat. #10711-018, Gibco BRL Life Technology, Gaithersburg, Md.); QIAexpress® Type VI Kit (Cat. #32149, Qiagen, Inc., Chatsworth, Calif.); IMPACT® I System (Cat. #6500, New England Biolabs, Inc., Beverly, Mass.).

EXAMPLE 2

Purification of Recombinant OPAA-2

Purification Procedure

A one liter culture of pTC6513/XL1-blue cells was grown to lag phase, harvested and then frozen. The frozen cells were resuspended in 10 BM buffer (10 mM Bis-Tris propane. 0.1 mM $MnCl_2$, pH 7.2) at a ratio of 3 ml of buffer for each gram of wet cells. The cells were sonicated for 2 minutes at 4° C. and the cellular debris removed by centrifugation. Approximately 200 mg of protein from the crude lysate was then used to prepare purified rOPAA-2.

To remove nucleic acids, four volumes of BPA1000 (TOSOHAAS, Montgomeryville, Pa.) was added to the lysate and the mixture was incubated at 4° C. for 10 min. The mixture was then centrifuged at 2,000×g for 5 min., resulting in a cell-free extract containing OPAA activity. Further purification of the enzyme through $(NH_4)_2SO_4$ fractionation, DEAE ion exchange chromatography and hydroxyapatite chromatography (HA-Ultrogel) was then followed by procedures similar to those described previously. (See Cheng et al., 1996 and DeFrank and Cheng, 1991.) The OPA anhydrolase activity of rOPAA-2 after each step of the purification scheme was determined using the following assay.

Assay for Enzyme Activity

OPAA activity for diisopropyl fluorophosphate (DFP) was assayed by monitoring released fluorine ion concentration with an ion-specific electrode (see Cheng et al., 1996 and DeFrank and Cheng, 1991). The reaction medium contained 3.0 mM DFP, BTP (500 mM NaCl, 50 mM Bis-tris propane, pH 7.2), 0.1 mM $MnCl_2$, and 2 to 25 µl of enzyme sample in a total volume of 2.5 ml. One unit of OPA anhydrolase activity catalyzes the release of 1.0 µmole of fluorine ion per min. at 25° C.

The specific activity of enzyme recovered after each purification step was calculated (µmole of F- released/min/ mg of protein). Protein concentrations were determined calorimetrically using a Coomassie blue assay (Pierce Co., Rockford, Ill.) with bovine serum albumin (BSA) as the standard.

As summarized in Table 1 below, this purification procedure provided an increase in specific activity of the rOPAA-2 enzyme of almost 20 fold. with a 9% recovery. The expressed enzyme constituted about 5% of the total cellular protein in the recombinant cells.

TABLE 1

Purification of OPA Anhydrolase-2 from Recombinant Cells.

| Purification Step | Total Volume (ml) | Total Protein (mg) | Total Activity (U) | Specific Activity (U/mg) | Purification | Yield |
|---|---|---|---|---|---|---|
| Crude Extract | 15.0 | 204.0 | 3060 | 15 | | 100 |
| BPA-1000 | 60.0 | 144.0 | 3070 | 21 | 1.4 | 100 |
| $(NH_4)_2SO_4$ (45–65%) | 5.2 | 58.2 | 3250 | 56 | 3.7 | 106 |
| DEAE-Sephacel | 6.0 | 7.3 | 770 | 105 | 7.0 | 25 |
| HA-Ultrogel | 1.9 | 0.9 | 270 | 300 | 20.0 | 9 |

*Protein and activity values are given as mean of triplicate for each of enzyme preparation.

EXAMPLE 3

Substrate Specificity of rOPAA-2

To evaluate the ability of rOPAA-2 to hydrolyze different OP compounds, the activity of the purified enzyme for DFP, GB, GD, GF and a chromogenic soman analog (NP-GD) was compared. OPA anhydrolase activity was assayed essentially as described above, with the exception that the hydrolysis of NP-GD was determined by monitoring the absorbance at 405 nm for p-nitrophenol (extinction coefficient, 10,101 at pH7.2). For all OP compounds tested, 0.1 to 3 mM of the OP substrate and 0.3 to 0.4 units of purified rOPAA-2 was used per 2.5 ml reaction.

The kinetic parameters for these OP compounds were determined by a progress curve fit with the Michaelis-Menten equation, using at least five different substrate concentrations per curve. The substrate concentrations used were between approximately 0.3 and 3 times the $K_m$. Other concentrations were used in initial range-finding experiments but were not included in the final calculations. Curve fitting was accomplished with the EZ-FIT software which uses the Nelder-Mead simplex and Marquardt nonlinear regression algorithms sequentially (Perella, F. W., "EZ-FIT: a practical curve-fitting microcomputer program for the analysis of enzyme kinetic data on IBM-PC compatible computers", *Anal. Biochem.*, Vol. 174, pp. 437–447, 1980, incorporated herein by reference).

Figure 1A:
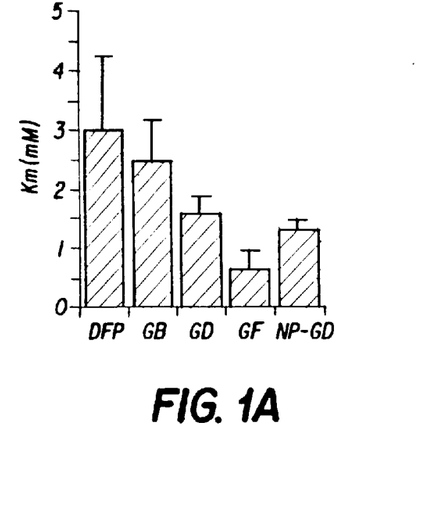
FIG. 1A is a graph of the Km values and FIG. 1B is a graph of the Vmax values.
Figure 1B:
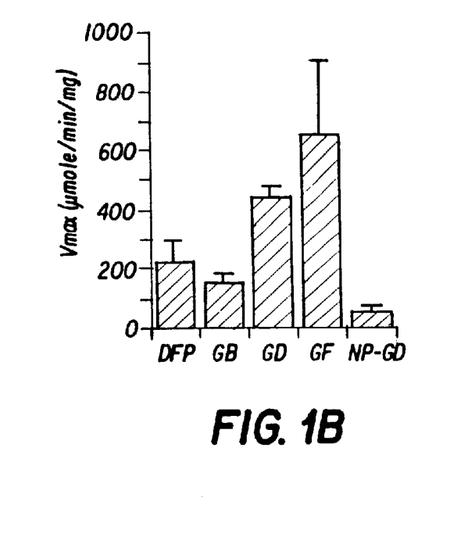
Figure 2:
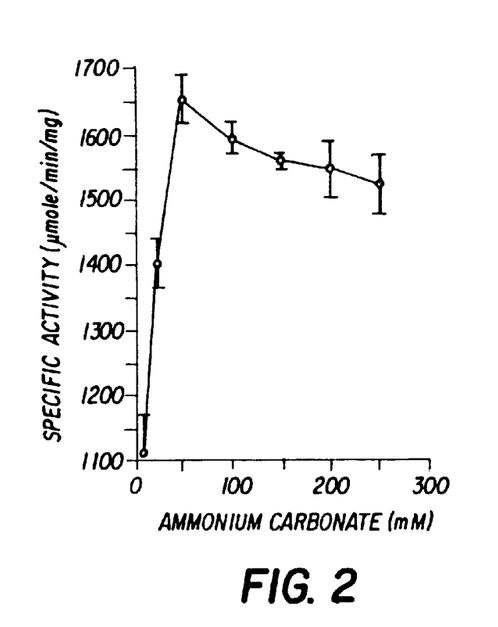
FIG. 2 shows the effect of varying the ammonium carbonate, $(NH_4)_2CO_3$, concentration on the specific activity of rOPAA-2.
Figure 3:
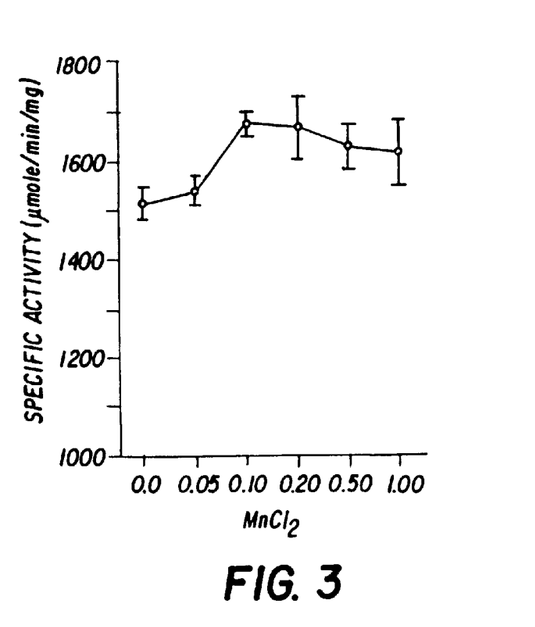
FIG. 3 shows the effect of varying the manganese chloride, $MnCl_2$, concentration on the specific activity of rOPAA-2 buffered in 50 mM $(NH_4)_2CO_3$.
Figure 4:
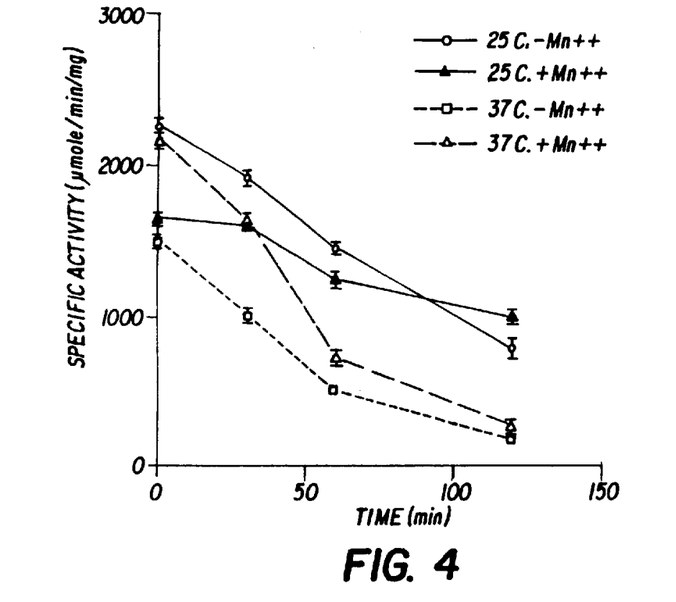
FIG. 4 shows the stability of rOPAA-2 in $(NH_4)_2CO_3$ buffer at 25° C. and 37° C.
Figures 5A, 5B:
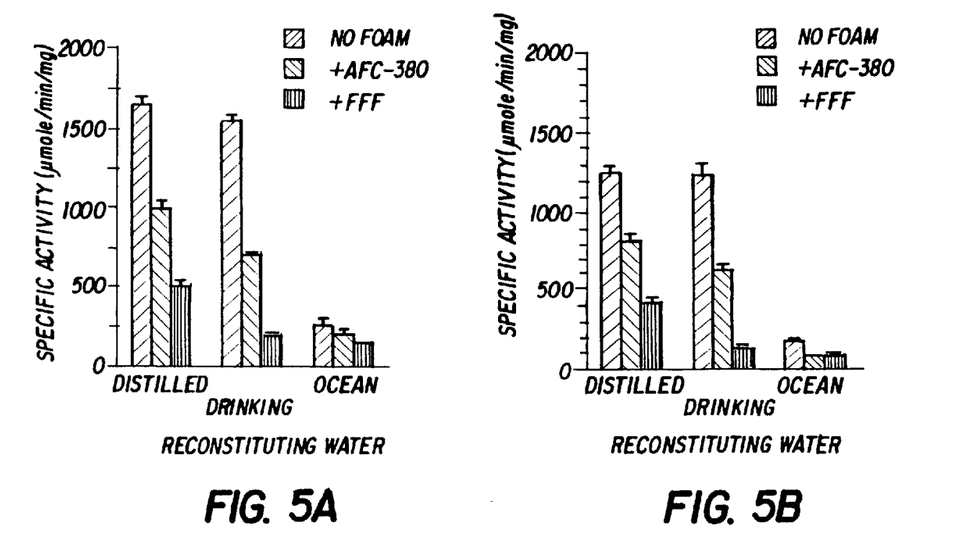
FIG. 5A is a bar graph of OPAA-2 activity at 0 min.
FIG. 5B is a bar graph of OPAA-2 activity at 60 min. after reconstitution, respectively.

As shown in FIG. 1, the apparent $K_m$ values for DFP, GB, GD, GF and the soman analog (NP-GD) were 2.99, 1.57, 2.48, 0.63 and 1.27 mM, respectively. Apparent $V_{max}$ values against these substrates were 230, 442, 151, 652, and 52 μmole/min/mg, respectively. The recombinant enzyme also hydrolyzes paraoxon at about 2% of the rate of DFP ($V_{max}$: 6.11 μmole/min/mg). Thus the purified recombinant OPAA-2 is capable of hydrolyzing DFP and a wide variety of chemical nerve agents under standard assay conditions.

To investigate the usefulness of rOPAA-2 for the detoxification of organophosphorus compounds under a variety of conditions that may be present under actual use conditions, the following experiments were performed.

EXAMPLE 4

The Effect of Reaction Conditions on rOPAA-2 Activity

The activity of purified rOPAA-2 for DFP was assayed under various reaction conditions, including different buffers, pH values, and temperatures. The results are shown in Table 2 below.

TABLE 2

Specific activity of rOPAA-2 With Various Assay Conditions.

| Assay Condition[a] | Specific Activity (μmol/min/mg) |
|---|---|
| BTP, pH 7.2 (standard condition) | 310.0 ± 11.7 |
| BTP, pH 7.2 + DTT[b] | 593.9 ± 36.4 |
| BTP, pH 7.2 + DTT[b] + BSA[c] | 309.8 ± 17.6 |
| BTP, pH 7.2 + DTT[b] + glycerol[d] | 325.8 ± 20.1 |
| BTP, pH 8.5 + DTT[b] | 713.4 ± 31.0 |
| BTP, pH 8.5 + DTT[b], 55° C. | 842.6 ± 7.1 |
| Na-acetate/NaOH, pH 8.5 | 398.7 ± 16.0 |
| $NH_4$-acetate, pH 6.80 | 451.6 ± 10.2 |
| $NH_4$-formate, pH 6.35 | 300.5 ± 19.8 |
| $NH_4$-chloride, pH 5.85 | 119.7 ± 3.1 |
| $NH_4$-acetate/NaOH, pH 8.50 | 2,405.7 ± 37.3 |
| $NH_4$-formate/NaOH, pH 8.50 | 2,373.5 ± 37.1 |
| $NH_4$-chloride/NaOH, pH 8.50 | 2,356.3 ± 113 |
| $(NH_4)_2$-carbonate/HCl, pH 8.50 | 2,064.7 ± 18.2 |
| $(NH_4)_2$-carbonate, pH 8.70 | 1,675.8 ± 23.2 |

[a]Assays performed as described in Example 2: all buffers at 50 mM final concentration, temperature at 25° C. unless indicated otherwise.
[b]DTT, 0.1 mM
[c]BSA, 0.5 mg/ml
[d]Glycerol, 50%

This experiment demonstrated that the specific activity of rOPAA-2 is affected by the assay conditions. For example, the addition of 0.1 mM DTT (dithiothreitol) to the standard assay buffer resulted in an approximately two-fold increase in specific activity of rOPAA-2 at pH 7.2 (compare rows 1 and 2). When the temperature and pH were raised 30 to 55° C. and 8.5 respectively, the specific activity of rOPAA-2 in the presence of DTT increased about 2.5-fold (compare rows 1 and 6). However, the most striking increases in specific activity occurred when the reaction buffer was changed from BTP to an ammonium-based buffer and the pH adjusted to pH 8.5 or greater (ammonium carbonate dissolved in distilled water has a pH value of around 8.6–8.7), with increases between 5- and 8-fold (compare row 1 with rows 11–15). These results suggest that rOPAA-2 is stimulated by the ammonium ion.

Since the rOPAA-2 showed a high level of anhydrolase activity when buffered with environmentally safe and inexpensive $(NH_4)_2CO_3$, the effect of varying the concentration of $(NH_4)_2CO_3$ was then studied. In this experiment, the reaction medium contained between 0 and 250 mM $(NH_4)_2CO_3$, 3.0 mM DFP, 0.1 mM $MnCl_2$, and 0.3–0.4 units of rOPAA-2 in a total volume of 2.5 ml. As shown in FIG. 2, rOPAA-2 exhibited a high level of OPA anhydrolase activity over a broad range of $(NH_4)_2CO_3$ concentrations, with activity being greatest at 50 mM $(NH_4)_2CO_3$.

The activity of rOPAA-2 for DFP in 50 mM $(NH_4)_2CO_3$, pH 8.7, with varying $MnCl_2$ concentrations was also investigated. The results of this experiment, which are shown in FIG. 3, demonstrate that rOPAA-2 is also active over a broad $MnCl_3$ concentration range, with the greatest OPA anhydrolase activity at ≧0.1 mM $MnCl_2$.

In addition to having OPA anhydrolase activity, it is desirable that an enzymatic detoxification agent meet several other criteria. For example, the enzyme solution needs to be stable for a time period sufficient to allow its application to the contaminated personnel, equipment or field, and to allow degradation of a significant amount of the contaminating OP compound(s). Also, to reduce the logistical burden of field application, the OPAA enzyme should have a long shelf life when packaged in a lyophilized form and be highly active when reconstituted with whatever water that is readily available when needed. Finally, the enzyme should be compatible with foam or spray systems commonly used in fire-fighting operations, since these systems are uncomplicated and useful for applying the enzyme to large areas. The ability of rOPAA-2 to meet these criteria was assessed in the following examples.

EXAMPLE 5

Stability of rOPAA-2 in $(NH_4)_2CO_3$ Buffer

Recombinant OPAA-2 was suspended in 50 mM $(NH_4)_2CO_3$ (pH 8.7) with or without 0.1 mM $MnCl_2$ and was incubated at 25° C. or 37° C. up to 120 min. and then assayed for activity against DFP as described in Example 1. The data from this experiment are shown in FIG. 4. The enzyme was more stable in the presence of $MnCl_2$ at both temperatures and had the highest initial activity at 37° C. in the presence of $MnCl_2$. However, because the enzyme exhibited a much smaller decrease in activity when incubated in the presence of $MnCl_2$ for 2 hours at 25° C. than when incubated for 2 hours at 37° C., it had the highest activity by the end of the incubation period. Thus, the stability of enzyme activity in $(NH_4)_2CO_3$-buffered solutions containing 0.05–1.0 mM $MnCl_2$ at temperatures around 25° C. is sufficient for practical applications. Moreover, $(NH_4)_2CO_3$ is an inexpensive and environmentally safe buffer.

EXAMPLE 6

Effect of Storage Conditions and Reconstitution Solutions on rOPAA-2 Activity

The enzyme was lyophilized in the presence or absence of 250 mM trehalose (α-D-glucopyranosyl-α-D-glucopyranoside) with either 5 volumes of a solution containing 50 mM $(NH_4)_2CO_3$, pH 8.7 and 0.1 mM $MnCl_2$ or, as a control, 5 volumes of 10 BM (10 mM Bis-Tris-propane. pH 7.2) containing 0.1 mM $MnCl_2$ and 0.1mM DTT (without trehalose). The lyophilized enzyme preparations were stored up to one year at various temperatures between −80° C. and +37° C. and then reconstituted in the presence or absence of 6% foam agent with 0.1 mM $MnCl_2$ and either BTP or $(NH_4)_2CO_3$ buffer (50 mM, pH 8.7) prepared with distilled water, municipal drinking water collected at Baltimore, Md. (approximately 1 mg/liter residual chlorine), or Atlantic Ocean water collected at Ocean City, Md. The foam agent used was either blast containment foam (AFC-3800) (Sandia National Laboratory, Albuquerque, N.M.) or fire-fighting foam (FFF) (Ansul Fire Protection Inc., Marinette, Wis.). The various reconstituted rOPAA-2 enzyme solutions were then assayed for OPA anhydrolase activity of DFP at 0 minutes or 60 minutes after reconstitution. There was no foam generation in these experiments.

Enzyme lyophilized with trehalose and $(NH_4)_2CO_3$ was found to be stable at −80° C. to +37° C. for up to a year with no apparent loss of activity (data not shown). The importance of trehalose in stabilizing the lyophilized enzyme preparations was demonstrated by the results with rOPAA-2 lyophilized with either $(NH_4)_2CO_3$ or 10 BM. Without trehalose, the enzyme lost >90% of its activity.

The effect of the source of the water used to prepare the various $(NH_4)_2CO_3$ reconstituting solutions on the activity of rOPAA-2 lyophilized in $(NH_4)_2CO_3$ and trehalose is shown in FIGS. 5A and 5B. Lyophilized enzyme reconstituted in the absence of foam with distilled water or drinking water did not differ with respect to OPA anhydrolase activity at either 0 min (FIG. 5A) or 60 min (FIG. 5B) after reconstitution. In contrast, lyophilized enzyme suspended in ocean water containing no foam exhibited less activity.

These results demonstrate that rOPAA-2 can be stored as a lyophilized powder in compact containers and reconstituted when needed with $(NH_4)_2CO_3$-buffer distilled water or $(NH_4)_2CO_3$-buffered drinking water to yield a enzyme solution with high OP-hydrolyzing activity.

In the presence of AFC-380, approximately 60% and 45% of the enzyme activity were retained in distilled water and drinking water, respectively, compared with the control with no foam agent. These activities are still higher than untreated enzyme assayed under standard conditions (BTP, pH 7.2 at 25°)(Table 1). In the presence of the other fire fighting foam (FFF) tested, only 30% and 15% of the activity was retained in $(NH_4)_2CO3$ -buffered distilled water and drinking water, respectively. When the lyophilized enzyme was reconstituted in $(NH_4)_2CO_3$ -buffered ocean water with or without foam agent, enzyme activities were greatly reduced by about 85–90%.

The effect of the reconstituting solution on the stability of the resulting enzyme solution is shown in FIG. 5B. One hour after reconstitution of the lyophilized enzyme with distilled or drinking water in the absence of foam, the enzyme activity decreased by approximately 25%. Enzyme reconstituted in the presence of either 6% AFC-380 or 6% FFF exhibited a decrease in activity of about 20% in one hour. These results demonstrate that an enzyme solution that is quite stable for at least one hour is produced when rOPAA-2, lyophilized in 250 mM trehalose, 50 mM $(NH_4)_2CO_3$, pH 8.7, and 0.1 mM $MnCl_2$, is reconstituted with 6% AFC-380 and $(NH_4)_2CO_3$-buffered water (either distilled or drinking water).

In contrast, a foam agent did not moderate the decrease in activity of the enzyme reconstituted with $(NH_4)_2CO_3$ -buffered ocean water. Without foam agent, the activity of the enzyme in ocean water decreased by 34% during the one hour period, while the presence of 6% AFC-380 or 6% FFF in the ocean water resulted in a decrease in activity over the same period of 60% and 47%, respectively.

The above results demonstrated the feasibility of a foam-based enzyme system for the detoxification of chemical nerve agents and related organophosphorus compounds. The activity of rOPAA-2 in a number of other foams, wetting agents and degreasers was also examined and is described in the following example.

EXAMPLE 7

Activity of rOPAA-2 in Various Biodegradable and Water Soluble Materials

In this experiment, rOPAA-2 non-lyophilized was assayed in distilled water containing 50 mM $(NH_4)_2CO_3$ and 0.1 mM $MnCl_2$ in the absence (control) or presence of one of various biodegradable and water soluble materials. The resulting enzyme solutions were assayed at 25° C. for OP-hydrolyzing activity using 3.0 mM DFP as the substrate and 0.3–0.4 units of rOPAA-2 in a total volume of 2.5 ml. The average of the results obtained in 3 assays for each substance are shown in Table 3 below.

TABLE 3

Specific activity of rOPAA-2 in biodegradable and water soluble materials.

| Material | Property | Conc. Used (%) | Sp. Activity (U/mg) |
|---|---|---|---|
| Control | N/A | N/A | 1950 |
| AFC-380 ® (Sandia Nat. Lab., Albuquerque, NM) | blast-containment foam | 6 | 1050 |
| FFF ® (3M. St. Paul, MN) | fire fighting foam | 6 | 460 |
| BioSolve ® (Westford Co., Westford, MA) | fire fighting wetting agent | 6 | 1030 |
| Cold Fire-Retardant ® (Firefreeze, Rockaway, NJ) | fire retarding agent | 10 | 3520 |
| Cold Fire ® (Firefreeze, Rockaway, NJ) | fire suppressing agent | 10 | 2340 |
| BV 406LF ® (Firefreeze, Rockaway, NJ) | degreaser/cleaner | 10 | 1430 |
| Odor Seal ® (Firefreeze, Rockaway, NJ) | wetting agent/odor removing | 10 | 1980 |
| Star Cleaning Miracle ® (Star, Hudsonville, MI) | wetting agent/oil removing | 30 | 670 |
| SC-1000 ® | wetting agent/degreaser | 5 | 650 |

TABLE 3-continued Specific activity of rOPAA-2 in biodegradable and water soluble materials.

| Material | Property | Conc. Used (%) | Sp. Activity (U/mg) |
|---|---|---|---|
| (Gemtek, Phoenix, AZ) Supersolve ® | wetting agent/degreaser | 10 | 440 |
| (Gemtek, Phoenix, AZ) Blue Base ® (Neutron, Torrance, CA) | degreaser | 8 | 140 |

These data indicate that the activity of rOPAA-2 is fairly stable or even enhanced in a number of these water soluble and biodegradable materials, including AFC-380, BioSolve, Cold Fire-Retardant, Cold Fire, BV 406LF, and Odor Seal. Since OP compounds are often oily in nature, the use of these environmentally safe materials in the decontamination system should assist in the solubilization of the chemical agents for enzyme action. Thus, the combination of one or more of these biodegradable materials with a composition comprising rOPAA-2 prepared in $(NH_4)_2CO_3$ buffer and preferably also comprising $Mn^{++}$ offers considerable potential as an enzyme-based detoxification system.

In conclusion. the present invention provides a recombinant DNA construct coding for OPAA-2, cells transformed with this construct, rOPAA-2 produced by these transformed cells, and compositions comprising rOPAA-2 which are useful for safe and efficient degradation of chemical nerve agents and other related organophosphorus compounds. While the preceding examples used rOPAA-2 produced by pTC513/XL1-blue cells, the term rOPAA-2 is intended to include polypeptides having the biological activity of OPAA-2 which are produced by other recombinant microorganisms.

Because rOPAA-2 can also catalyze the hydrolysis of pesticides, a composition comprising rOPAA-2 may also be used to decontaminate agricultural equipment, remediate contaminated soils, and treat waste water generated from production facilities.

The composition may also comprise $MnCl_2$ for enhanced stability. In addition, the composition may be used at higher temperatures for higher OPAA-2 activity.

The composition may be incorporated with a foam, wetting agent or degreaser prior to application to aid in the application of the composition and solubilization of organophosphorus compounds. The resulting mixture may be applied to the surface to be decontaminated either manually or with a foam or spray system. Foam and spray systems are uncomplicated and have been used extensively for firefighting operations for many years.

Applying the rOPAA-2 composition with foam offers the advantage that the foam would act as a "blanket" to retard evaporation and shield the enzyme from inhibitory environmental elements. In addition, foam could also stabilize the enzyme and thus prolong its activity in the field. Because this foam-based detoxification system would not jeopardize user safety or harm the environment, it could be applied topically to personnel, equipment, agricultural fields or other large areas contaminated with OP compounds.

While the foregoing invention has been described in some detail by way of illustration and example for purposes of clarity of understanding, it will be obvious that certain changes and modifications may be practiced within the scope of the appended claims.

What is claimed is:

1. A composition for hydrolyzing organophosphorus compounds comprising an ammonium ion and an organophosphorus acid anhydrolase 2, OPAA-2, of Alteromonas, produced by a host cell transformed by a recombinant DNA construct for the expression of OPAA-2 in prokaryotic cells, said construct comprising a prokaryotic promoter operatively linked to a DNA fragment comprising a nucleotide sequence coding for a polypeptide having the biological activity of organophosphorus acid anhydrolase 2 of Alteromonas.

2. A composition according to claim 1, wherein the ammonium ion is provided by $(NH_4)_2CO_3$.

3. A composition according to claim 2, wherein the $(NH_4)_2CO_3$ is present at a concentration of between 25 mM and 250 mM.

4. A composition according to claim 3, wherein the $(NH_4)_2CO_3$ is present at a concentration of 50 mM.

5. A composition according to claim 1, further comprising $Mn^{2+}$ ions.

6. A composition according to claim 5, wherein the $Mn^{++}$ ions are provided by $MnCl_2$.

7. A composition according to claim 6, wherein the $MnCl_2$ is present at a concentration between 0.01 mM and 1.00 mM.

8. A composition according to claim 1, which is in a lyophilized form and further comprises trehalose.

9. A composition according to claim 1, further comprising at least one biodegradable, water soluble material selected from the group consisting of foams, wetting agents and degreasers.

10. A composition according to claim 9, wherein the biodegradable, water soluble material is AFC-380, BioSolve, Cold Fire-Retardant, Cold Fire, BV 406LF, or Odor Seal.

11. A composition according to claim 9, further comprising $MnCl_2$ at a concentration between 0.01 mM and 1.00 mM, wherein the organophosphorus acid anhydrolase 2, OPAA-2, of Alteromonas is present at a concentration of 0.12–0.16 units/ml and the ammonium ion is provided by $(NH_4)_2CO_3$ present at a concentration of between 25 mM and 250 mM.

12. A method for hydrolyzing organophosphorus compounds present on a surface or within a substance which comprises applying a solution to the surface or the substance and allowing sufficient time for hydrolysis of the organophosphorus compounds, wherein said solution comprises an ammonium ion and an organophosphorus acid anhydrolase 2, OPAA-2, of Alteromonas, produced by a host cell transformed by a recombinant DNA construct for the expression of OPAA-2 in prokaryotic cells, said construct comprising a prokaryotic promoter operatively linked to a DNA fragment comprising a nucleotide sequence coding for a polypeptide having the biological activity of organophosphorus acid anhydrolase 2 of Alteromonas.

13. A method according to claim 12, wherein the solution of an ammonium ion and organophosphorus acid anhydrolase 2, OPAA-2 of Alteromonas, further comprises $Mn^{2+}$ ions.

14. A method according to claim 12, comprising preparing a mixture of the solution and at least one biodegradable and water soluble material selected from the group consisting of foams, wetting agents and degreasers before the applying step.

15. A method according to claim 14, wherein the biodegradable and water soluble material is selected from the group consisting of AFC-380®, BioSolve®, Cold Fire-Retardant®, Cold Fire®, BV 406LF®, and Odor Seal®.

16. A method according to claim 14, wherein the mixture is applied to the surface or substance with a foam or spray system.

17. A method according to claim 12, wherein the solution is prepared by reconstituting a lyophilized composition comprising organophosphorus acid anhydrolase 2, OPAA-2, of Alteromonas, in an ammonium-buffered water.

18. A method according to claim 17, wherein the lyophilized composition further comprises $(NH_4)_2CO_3$, $MnCl_2$ and trehalose.

19. A method of detoxifying stocks of organophosphorus compounds, comprising adding to said stocks a composition comprising an ammonium ion and an organophosphorus acid anhydrolase 2, OPAA-2, of Alteromonas, produced by a host cell transformed by a recombinant DNA construct for the expression of OPAA-2 in prokaryotic cells, said construct comprising a prokarvotic promoter operatively linked to a DNA fragment comprising a nucleotide sequence coding for a polypeptide having the biological activity of organophosphorus acid anhydrolase 2 of Alteromonas.

20. The method of claim 19, wherein said composition further comprises $Mn^{2+}$ ions.

21. The method of claim 20, wherein said $Mn^{2+}$ ions are provided by $MnCl_2$.

* * * * *